United States Patent [19]

Butt

[11] Patent Number: 5,372,037

[45] Date of Patent: Dec. 13, 1994

[54] SOIL SAMPLING APPARATUS

[76] Inventor: Edward G. Butt, 3 E. Papago, Box 87, Bagdad, Ariz. 86321

[21] Appl. No.: 996,960

[22] Filed: Dec. 23, 1992

[51] Int. Cl.⁵ ............................................. E21B 49/02
[52] U.S. Cl. ................... 73/153; 73/863.57; 73/863.52
[58] Field of Search ............... 73/153, 863.52, 863.57, 73/863.54; 175/58, 60

[56] References Cited

U.S. PATENT DOCUMENTS

| 850,293 | 4/1907 | Calkins | 73/863.52 |
|---|---|---|---|
| 1,001,129 | 8/1911 | Fairchild | 73/863.54 |
| 1,521,545 | 12/1924 | Kistler | 73/863.41 |
| 1,642,337 | 9/1927 | Gray et al. | 73/863.54 |
| 1,679,064 | 7/1928 | Stephenson | 73/863.52 |
| 1,721,126 | 7/1929 | Lilligren | 175/88 |
| 3,241,371 | 3/1966 | Horeth | 73/863.57 |
| 3,735,641 | 5/1973 | Bink et al. | 73/863.43 |
| 4,218,920 | 8/1980 | John, Jr. | 73/433 |
| 4,307,385 | 12/1981 | Evans et al. | 73/647 |
| 4,317,378 | 3/1982 | Mustard | 73/863.52 |
| 4,718,289 | 1/1988 | Barrett | 73/153 |
| 4,783,995 | 11/1988 | Michel et al. | 73/151 |
| 4,918,999 | 4/1990 | Wenshau et al. | 73/863.54 |

Primary Examiner—Robert J. Warden
Assistant Examiner—Hien Tran
Attorney, Agent, or Firm—Richard C. Litman

[57] ABSTRACT

A sampler gathers a portion of borehole cuttings being discharged during a mining drilling operation. The unconfined cuttings are discharged over the sampler while falling to ground surface surrounding the borehole. The sampler diverts a small portion of the flow over two receptacles which are sized to hold a desired volume of cuttings. The receptacles shuttle back and forth over a discharge chute, periodically depositing the desired volume of cuttings into a cuttings container, for subsequent chemical analysis to determine the nature of the ore. A signal derived from the drillstring shaft revolution rate controls the receptacles, so that a sampling is taken at regular drilling depth intervals. A constant, small sample is thus held aside for analysis which is more representative of the soil strata than is a sample obtained by a conventional manual coring operation.

18 Claims, 5 Drawing Sheets

SOIL SAMPLING APPARATUS

BACKGROUND OF THE INVENTION

1. Field of the Invention

The present invention relates to a sampler which intercepts a stream of fluent material and removes a portion thereof for subsequent analysis.

2. Description of the Prior Art

Samplers have long been employed to remove periodically a fraction of particulate, fluent material from a stream to facilitate monitoring the characteristics of that material. In manufacturing processes, or in other situations in which the material stream flows in a conduit, this is a relatively easy matter. However, in exploiting underground mineral deposits, the sampling procedure must take place in situ, and is affected by the environment, weather, and other variables which threaten the orderly recovery of sample specimens.

In open pit copper mining, sampling requires drilling a plurality of exploratory boreholes in exposed soil within the pit, obtaining soil specimens from these boreholes, and analyzing the specimens to determine a preferred approach to the economical exploitation of copper ore. The conventional method of sampling is to sink a hand held tube into a mound of borehole cuttings that has been discharged onto the surrounding ground, and thus obtain a core which is assumed to be representative of geological strata into which the borehole has been drilled.

While this method is simple and inexpensive, it is notoriously unreliable in that a cuttings mound disposed on surrounding ground is frequently not representative of the strata from whence it originated. This is due to uneven deposition of cuttings on the ground immediately following discharge from the borehole. Uneven deposition arises from uneven ground, which may include rocks and boulders, shifting wind patterns in the area of discharge from the borehole, and similar conditions beyond the control of the drill operator. Critical assumptions as to the characteristics of the strata are thus frequently founded on poor data.

The following patents are cited to illustrate generally samplers which intercept a stream of fluent material.

U.S. Pat. Nos. 1,001,129, issued to O. H. Fairchild on Aug. 22, 1911; 1,642,337, issued to O. H. Gray et al. on Sep. 13, 1927, 1,679,064, issued to S. E. Stephenson on Jul. 31, 1928, and 3,735,641, issued to Werner R. Bink et al. on May 29, 1973, all disclose diversion apparatus, such as a chute, for intercepting a stream of fluent material.

U.S. Pat. Nos. 1,521,545, issued to W. D. Kistler on Dec. 30, 1924, 1,721,126, issued to J. M. Lilligren on Jul. 16, 1929, and 4,918,999, issued to Hugo Wenshau et al. on Apr. 24, 1990, include sample collection means operating in conjunction with diversion apparatus.

U.S. Pat. No. 4,218,920, issued to Clarence D. John on Aug. 26, 1980, discloses a carrying receptacle which shuttles between a stream of fluent material and a measuring device.

While the aforementioned inventions and patents disclose samplers which are effective given their respective specific applications, there remains a need for a soil sampler which is operable in an uncontrolled environment, which samples an unconfined stream of fluent material, and which does not expose delicate machine elements, such as gears, worm drives, and the like to dust and dirt. Thus, none of the above inventions and patents, taken either singly or in combination, is seen to describe the instant invention as claimed.

SUMMARY OF THE INVENTION

The present invention provides a soil sampling apparatus suitable for determining the nature of geological strata during drilling of an exploratory borehole. The sampling apparatus, which takes specimens at regular and frequent intervals, is configured and located to sequester a soil specimen immediately upon discharge from the borehole. It operates in an uncontrolled environment, and successfully recovers suitable samples from an unconfined discharge stream.

A dual pocket receptacle sits inside a housing having an inlet orifice located in a top wall thereof and two discharge orifices located in its floor. The dual pocket receptacle shuttles between a right and a left position, each pocket thus being positioned alternately below the inlet orifice and above a discharge orifice. The receptacle is moved by fingers which are actuated by prime movers, such as solenoids, pneumatic cylinders, or the like.

The housing is mounted on a drilling rig so as to be disposed in the path of a plume of discharged borehole cuttings, which are transported from the borehole pneumatically. The sampling apparatus is partially covered by discharged cuttings, a portion of which falls into the housing, and then into the dual pocket receptacle. The pockets have no floor, and upon aligning with the discharge orifices, the sample is discharged into a container. This container, which is periodically removed for analysis, progressively fills with cuttings.

Sampling at constant drilling depth intervals is assured by a signalling system employing magnets placed on a rotating part of the drilling rig. As a magnet passes a magnetically responsive switch, a signal is generated which causes the prime mover to operate the fingers. In a preferred embodiment, an electronic control circuit enables most of the signalling system to operate at 5 VDC.

Since a predetermined relation between drill shaft rotation and vertical drilling penetration exists in typical drilling rigs used in open pit copper mining, magnets can be located on the rotating part so as to time shuttling with predetermined drilling depth intervals.

The sample container is thus filled with soil in a manner representative of the geological strata. The soil sampling apparatus is suited for collection of samples from an irregular and unconfined plume of discharged material, and has no parts susceptible to jamming that are exposed to dust and dirt.

Accordingly, it is a principal object of the invention to provide a sampling apparatus which intercepts a stream of fluent material being discharged to the open atmosphere prior to the material being deposited on the ground.

A second important object of the invention to provide a sampling apparatus which draws samples from an unconfined and irregular stream of fluent material.

It is a further object of the invention to provide a sampling apparatus which draws samples on a periodic basis with respect to drilling depth.

Another object of the invention is to provide a sampling apparatus which is unencumbered by machine elements which are exposed to dust.

Still another object of the invention is to provide a sampling apparatus which is operated by low voltage DC electrical power.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
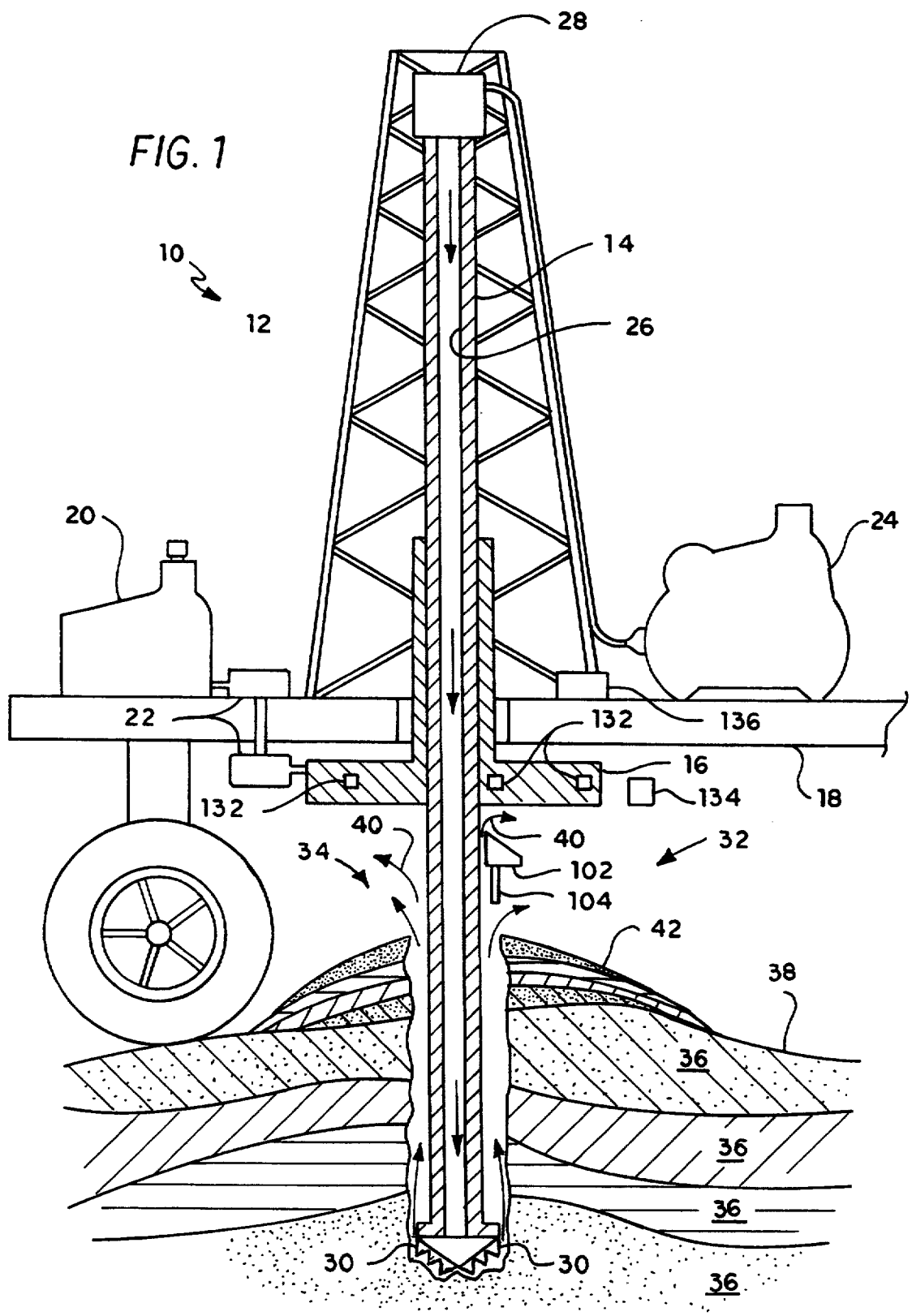
FIG. 1 is an environmental side elevational view of the invention, with drilling equipment and a geological ground formation shown substantially in cross section.

The present invention is seen in FIG. 1 in its environment. A truck mounted drilling rig 10 includes a derrick 12 which supports and steadies a drillstring 14; a turntable 16 or similar apparatus which grips and rotates the drillstring 14 by well known apparatus which will not be detailed further herein; and a truck platform 18. Disposed on the truck platform 18 are a diesel engine 20 which powers the turntable 16 through suitable transmission means such as gearboxes 22, and a source 24 of compressed air. Compressed air is introduced into a drillstring core 26 by means of a swivelling fitting 28. It is common in mining to employ compressed air to clean a cutting head 30 by blasting cuttings 32, or soil comminuted by drilling, therefrom, to cool the cutting head 30, and to transport cuttings 32 from the borehole 34, and apparatus to accomplish the same is well known in the art.

The novel so sampling apparatus 100 (see FIGS. 3A and 3B) includes a sequestering unit 102 mounted from the truck platform 18 by a suitable bracket (not shown) and a sample holding container 104, secured beneath the sequestering unit 102 also by a suitable bracket (not shown).

Drillstring 14 progresses through geological strata 36, creating borehole 34, as cutting heads 30 comminute the strata 36, cuttings 32 thus produced being transported to the ground surface 38 by the same compressed air which cleans and cools cutting heads 30. Cuttings 32 are ejected from the borehole 34 under considerable pressure, forming an unconfined, airborne stream 40, and are deposited on the ground surface 38, forming a mound 42 surrounding borehole 34.

This mound 42 has traditionally been sampled by a manual coring operation, but samples obtained thereby suffer from being rendered unrepresentative of ground from which they are obtained because of variables altering the orderly deposition on surrounding ground. The present invention eliminates much of the error introduced in conventional sampling by intercepting ejected soil 32 shortly after ejection from the borehole 34, and before wind and uneven ground cause unrepresentative deposition on the ground surface 38.

The sequestering unit 102 is therefore suspended from the truck platform 18 proximate the drillstring 14, in the unconfined airborne stream 40 of cuttings 32, and as close to the mound 42 of cuttings 32 as is feasible. Cuttings 32 are ejected upwardly from the borehole 34, and a portion thereof will come to rest on the sequestering unit 102. This portion is captured by the sequestering unit 102 and collected in the sample container 104 disposed directly beneath sequestering unit 102.

Operation of sequestering unit 102 will now be discussed, with reference to FIGS. 2A and 2B. Sequestering unit 102 comprises a housing 106 having one entry orifice 108 located in the top 110 of housing 106, and two discharge orifices 112 located in a bottom wall 114 thereof. A receptacle 116 is slidably confined within housing 106. The receptacle 116 has two chambers 118 having lateral walls 120, but lacking top or bottom walls, thus defining entry and discharge openings 122, 124 therein. Periodic alignment of appropriate orifices 108, 112 and openings 122, 124 provides a valve arrangement discharging cuttings 32 to sample container 104, and is accomplished as follows.

Figure 2A:
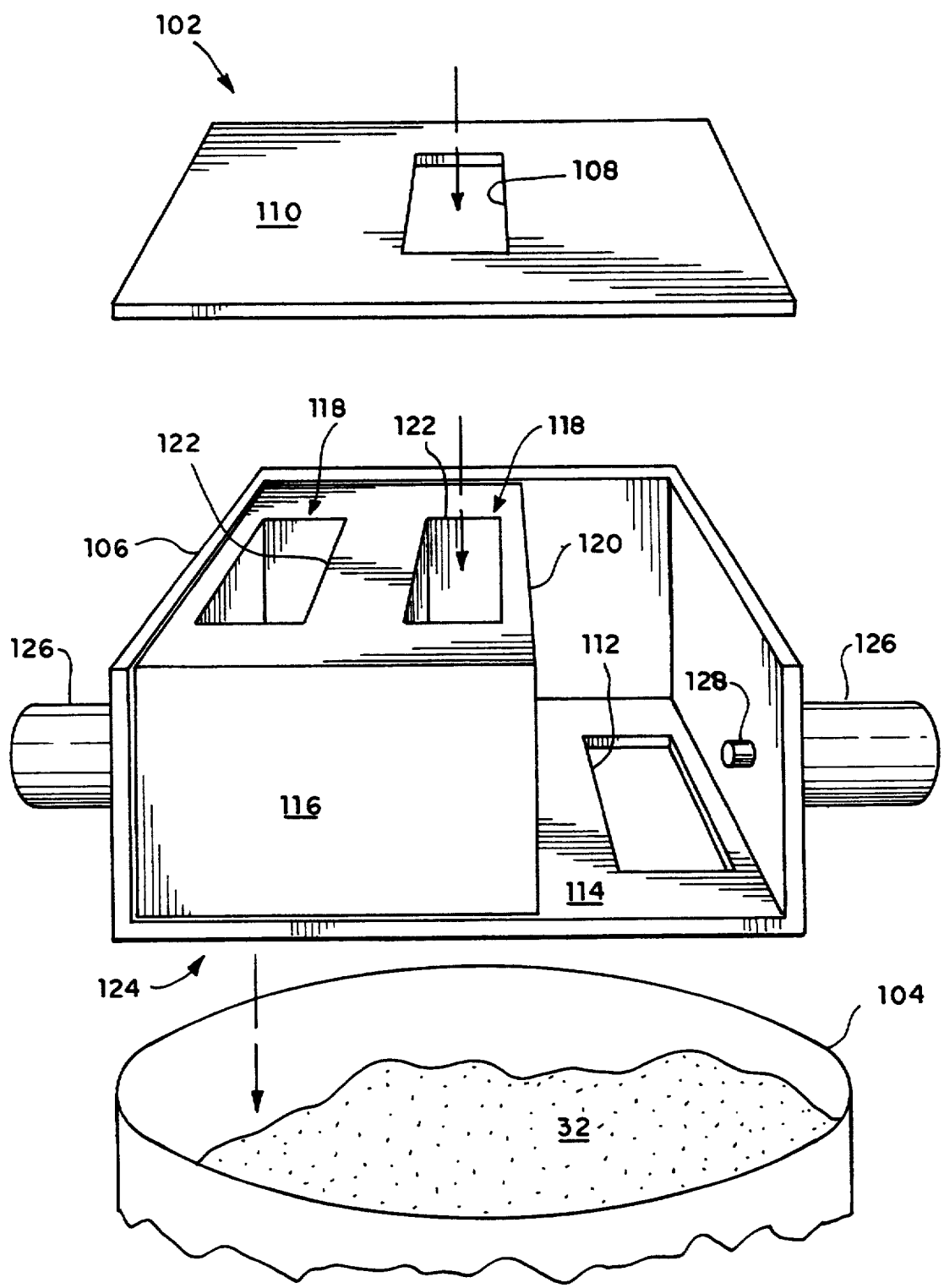
FIG. 2A and 2B are exploded perspective detail views of the sequestering unit, drawn to an enlarged scale.
Figure 2B:
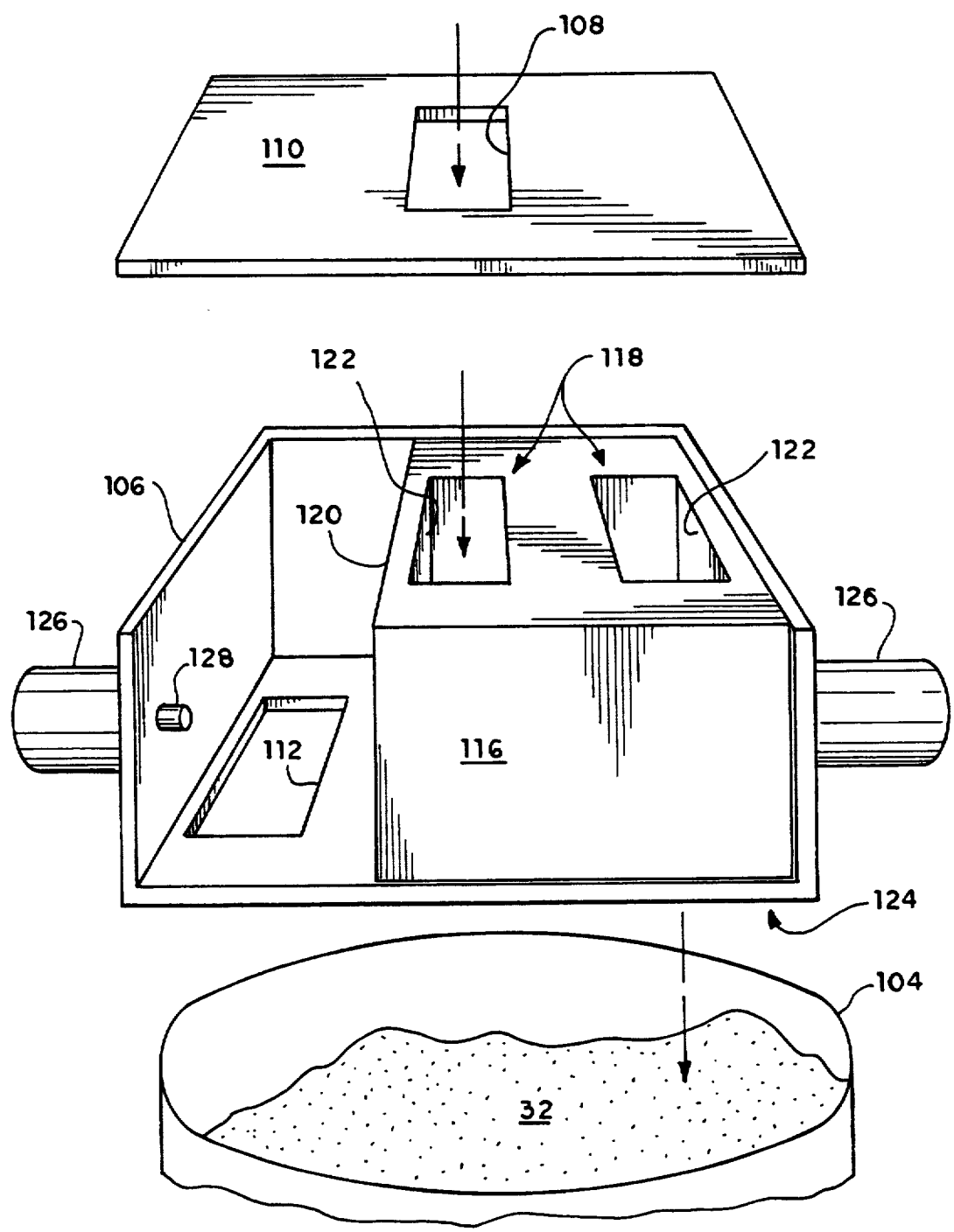

Receptacle 116 is shuttled back and forth, reciprocating between left and right positions (FIGS. 2A and 2B, respectively). This motion is imparted by two servomechanisms 126 actuating linkages comprising fingers 128. Receptacle 116 is thus positioned to receive cuttings 32 falling through entry orifice 108 into one chamber 118, and to discharge cuttings 32 previously collected in the other chamber 118 through discharge orifice 112 into sample container 104 below.

Servomechanisms 126 are controlled to move receptacle 116 in proportion to vertical drilling progress by a control circuit 130. Referring again to FIG. 1, magnets 132 are seen to be mounted on the rotating turntable 16 so as to pass periodically by a magnetically responsive reed switch 134. Since the rate of vertical drilling progress correlates to drillstring revolution rate in a known relationship, the number of magnets 132 is selected to cause reciprocation of receptacle 116, and hence to take one sample, for every three inches of vertical drilling progress.

Figure 3A:
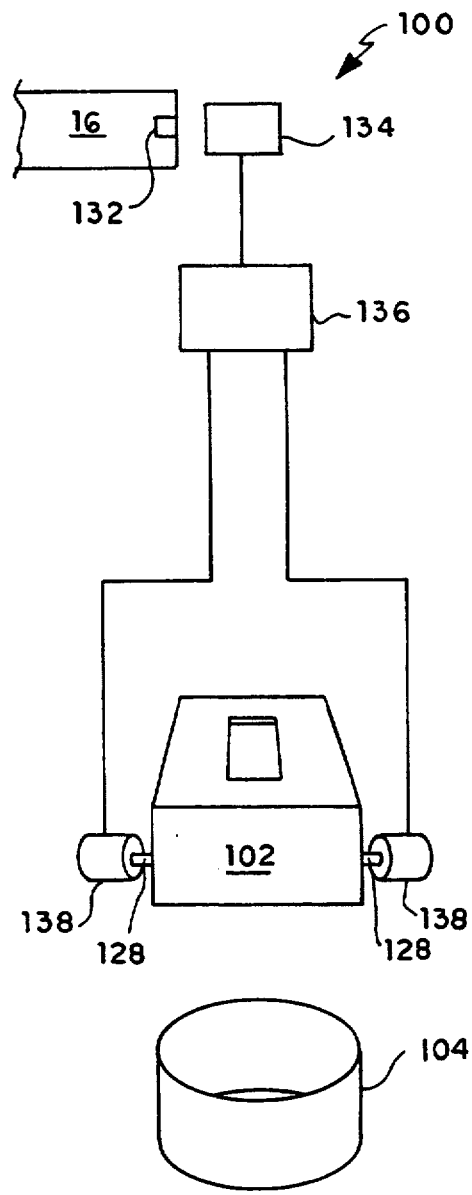
FIGS. 3A and 3B are diagrammatic views of alternative embodiments of the invention.

Turning now to FIG. 3A, reed switch 134 is connected to a control unit 136, which in turn is connected to servomechanisms 126. In an alternative embodiment of the invention illustrated in FIG. 3A, servomechanisms 126 comprise solenoids 138. Control unit 136 receives an input signal from reed switch 134, and sends signals alternately operating solenoids 138.

Figure 3B:
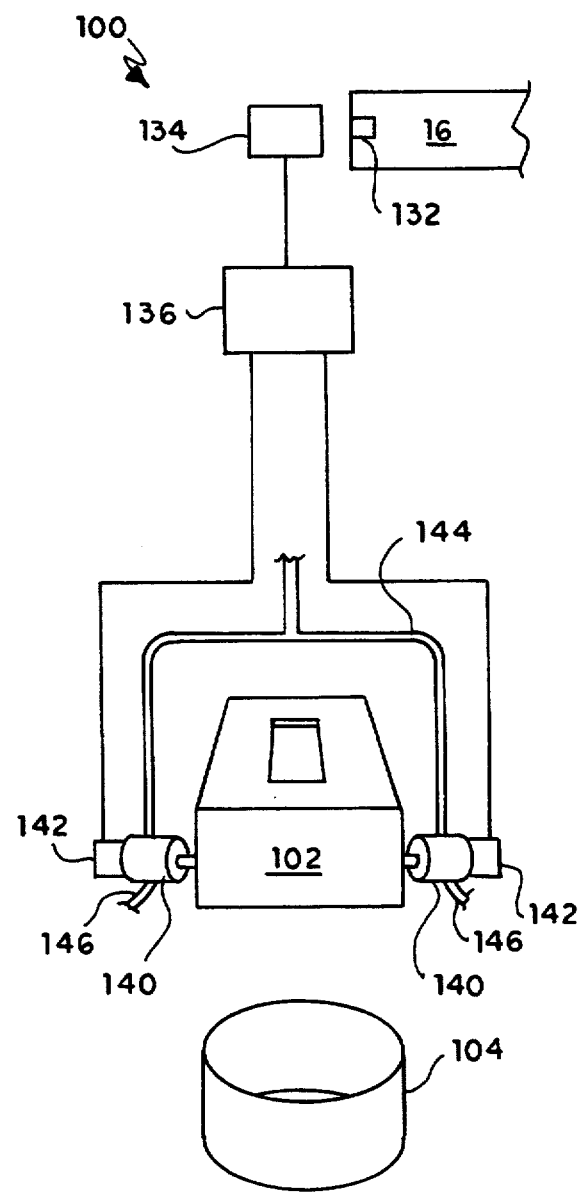

In an alternative embodiment, shown in FIG. 3B, servomechanisms 126 comprise pneumatic cylinders 140. The same signalling arrangement as formerly employed to operate solenoids 138 is usable to operate air valves 142. Air flowing in a supply conduit 144 from air supply 24 acts on pneumatic cylinders 140 in a well known fashion to cause fingers 128 to move as in the arrangement employing solenoids 138. This air is periodically vented through discharge conduits 146 to the atmosphere. Operation characteristics of sequestering unit 102 are thus unaffected, other than employing a different motive power source.

Figure 4:
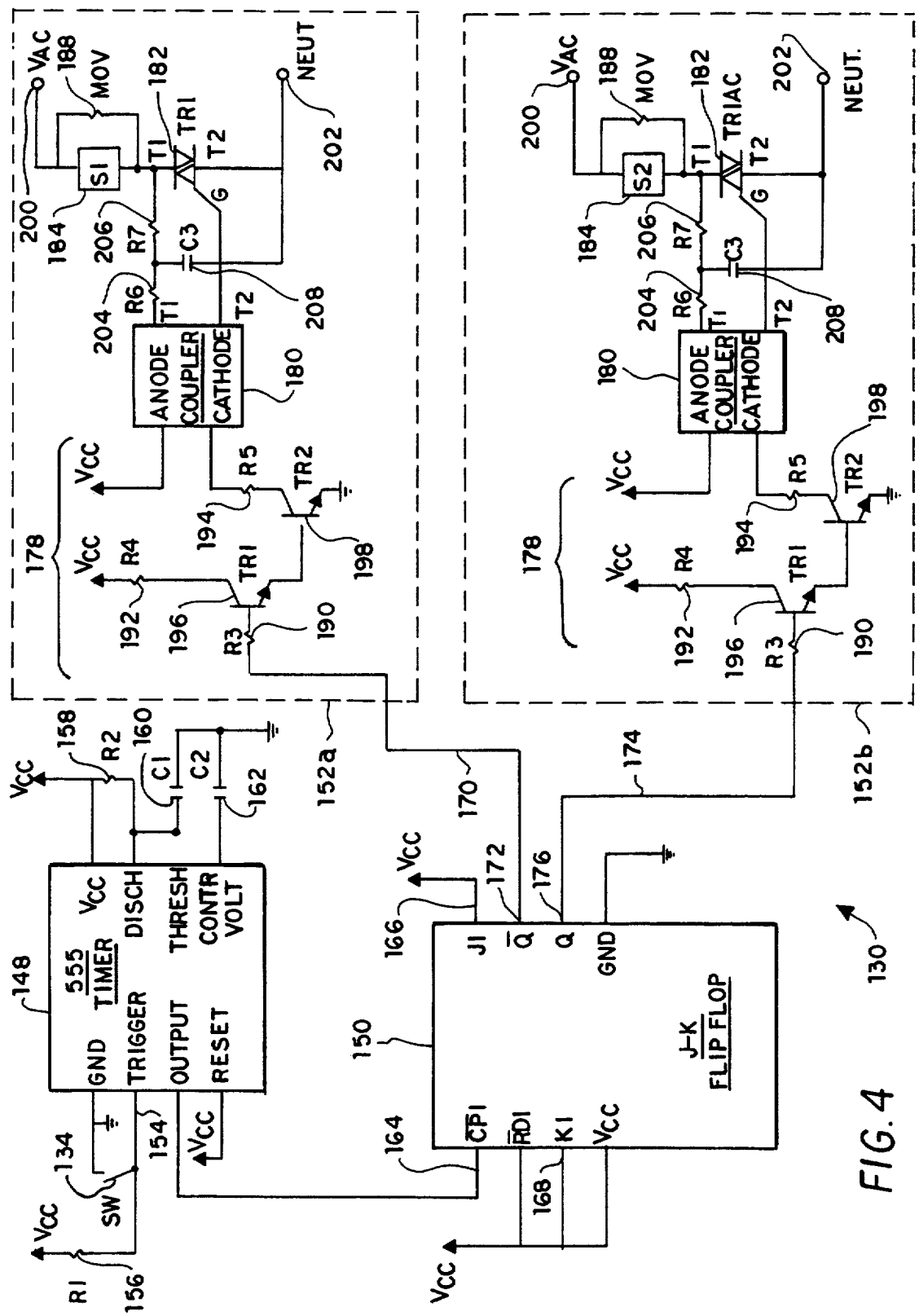
FIG. 4 is a schematic detail view of the control circuit of a preferred embodiment of the invention.

Low voltage DC electrical power, which is inherently safe and which enables inexpensive components to be employed in its regulation, is used in a preferred control circuit 130 described hereinafter, with reference being made to FIG. 4.

In the preferred control circuit 130, a 555 timer 148 accepts an input signal generated by closure of reed switch 134, and, after a predetermined time delay, enables a J-K flip flop 150 (hereinafter referred to as a JKFF 150), which in turn alternately energizes one of two identical servomechanism subcircuits 152A, 152B. At a trigger input 154, control circuit power $V_{cc}$ is maintained until reed switch 134 is closed, thereby producing a ground potential at the trigger input 154. Resistor R1 156 limits current flowing through reed switch SW 134.

Once a ground potential is present at the trigger input 154, the 555 timer 148 is activated, and starts to measure a predetermined time interval. This time interval is set in a conventional manner by selecting appropriate values for a resistor R2 158 and capacitors C1,02 160,162. With the connection of the 555 timer 148 to other components of the control circuit 130 being shown, function of 555 timers in general is well known, and internal circuitry thereof will not be discussed.

At the end of this time interval, an output signal is generated and transmitted to an enabling input Q 164 of the JKFF 150. Both the J1 and K1 inputs 166, 168 of the JKFF 150 are set in a conventional manner as to cause the JKFF 150 to toggle when enabled.

The input 170 to first subcircuit 152A is connected to the inverted output Q 172 of the JKFF 150, and the input 174 to second, identical subcircuit 152B is connected to the non-inverted output Q 176 of the JKFF 150.

Subcircuits 152A, 152B each is seen to include a Darlington pair 178 amplifying a current received from the JKFF 150. The amplified current then drives a coupler 180, thus enabling coupler 180 to drive a triac 182. When activated, triac 182 allows current from a separate, higher voltage, AC source to energize a solenoid coil 184 of a servomechanism 126. The solenoid coil 184 is protected from current surges by a varistor MOV 188.

Resistors R3, R4, and R5 190, 192, 194 are selected to bias each transistor TR1 and TR2 196, 198 of the Darlington pair 178.

Coupler 180 is a photocoupler, which acts in well known fashion to allow a DC input to regulate an associated AC output connected to terminals $V_{AC}$ 200 and NEUT 202.

Triac 182 is regulated in the following manner. A gate current sufficient to activate triac 182 is produced when coupler 180 is activated. Impedance values of resistors R6, R7 204, 206 and capacitor C3 208 are selected such that the following conditions are met. The value of the combined impedance of resistor R6 204 and capacitor C3 208 is low enough to produce this sufficient gate current when the coupler 180 is activated. The value of the combined impedance of solenoid coil 184, resistor R7 206, and capacitor C3 208 is high enough to prevent solenoid coil 184 from being activated by a current flowing therethrough unless triac 182 is activated.

The above described control circuit 130 enables a five volt DC power circuit to satisfy $V_{cc}$, and a nominal 120VAC circuit to cooperate therewith, and thus drive solenoids 138.

It is to be understood that the present invention is not limited to the embodiments described above, but encompasses any and all embodiments within the scope of the following claims.

I claim:

1. A soil sampling apparatus usable with a drilling rig having a rotating drill for boring a borehole in soil and producing drilling cuttings, said soil sampling apparatus comprising:
   sample container;
   sequestering means communicating with said sample container for receiving drilling cuttings, said sequestering means said sequestering means including a multi-chamber receptacle defining a plurality of receptacle chambers for holding the drilling cuttings, each of said receptacle chambers having a lateral wall, a top opening and a bottom opening, said sequestering means further including a housing surrounding said multi-chamber receptacle, said housing defining a top orifice communicating with said receptacle chambers and a bottom orifice communicating with said receptacle chambers and said sample container, said sequestering means and said sample container positioned so the drilling cuttings pass from said sequestering means to said sample container;
   actuating means for moving said receptacle between a first position wherein at least one of said receptacle chambers collects cuttings and a second at least one of said receptacle chambers discharges cuttings and a second position wherein said second at least one of said receptacle chambers collects cuttings and said at least one of said receptacle chambers discharges cuttings;
   signalling means for generating a signal responsive to a penetration depth of a rotating drill into soil, whereby portions of the drilling cuttings are progressively deposited in said sample container as the drill progresses downwardly into the soil.

2. The soil sampling apparatus according to claim 1, said actuating means comprising linkage means for moving said multi-chamber receptacle in reciprocating fashion.

3. The soil sampling apparatus according to claim 2, said actuating means further comprising a servomechanism acting on said linkage means.

4. The soil sampling apparatus according to claim 3, wherein said servomechanism comprising a solenoid.

5. The soil sampling apparatus according to claim 3, said servomechanism comprising a pneumatically powered cylinder.

6. The soil sampling apparatus according to claim 2, said signalling means comprising:
   a magnet arranged to rotate in proportion to vertical drilling progress, and
   a magnetically responsive switch disposed in operably close proximity to said magnet and supported on a drilling rig.

7. The soil sampling apparatus according to claim 6, said signalling means further comprising:
   a control unit receiving an input signal from said magnetically responsive switch and generating alternating signals responsively thereto, said alternating signals operating said actuating means.

8. The soil sampling apparatus according to claim 3, said signalling means comprising:
   a 555 timer connected to a DC power source,
   a magnetic reed switch completing a circuit to said 555 timer, thereby activating said 555 timer to produce an output signal,
   a J-K flip flop connected to said 555 timer such that said 555 timer output signal causes said J-K flip flop to toggle, and means for actuating said servomechanism, thereby causing said multi-chamber receptacle to move laterally in reciprocating fashion.

9. A soil sampling apparatus for use with a drilling rig having a rotating drill for boring a borehole in soil and producing drilling cuttings, said soil sampling apparatus comprising:
- a housing including a top orifice and a plurality of bottom orifices;
- a reciprocating, multi-chamber receptacle movably located within said housing and defining a plurality of receptacle chambers, each of said receptacle chambers having a top opening and a bottom opening;
- a sample container in communication with each of said receptacle chambers of said multi-chamber receptacle, said sample container and said multi-chamber receptacle positioned so drilling cuttings pass from said multi-chamber receptacle to said sample container;
- control means for controlling the reciprocation of said multi-chamber receptacle within said housing;
- a receptacle actuator responsive to said control means and moving said multi-chamber receptacle within said housing.

10. The soil sampling apparatus of claim 9, wherein said receptacle actuator comprises at least one servomechanism.

11. The soil sampling apparatus of claim 10, wherein said at least one servomechanism includes a first servomechanism for moving said multi-chamber receptacle to a first position wherein at least one of said receptacle chambers collects cuttings and a second at least one of said receptacle chambers discharge cuttings and a second servomechanism for moving said multi-chamber receptacle to a second position wherein said second at least one of said receptacle chambers collects cuttings and said at least one of said receptacle chambers discharges cuttings.

12. The soil sampling apparatus of claim 9, wherein said receptacle actuator further comprises at least one pneumatic cylinder.

13. The soil sampling apparatus of claim 12, wherein said at least one pneumatic cylinder includes a first pneumatic cylinder for moving said multi-chamber receptacle to a first position wherein at least one of said receptacle chambers collects cuttings and a second at least one of said receptacle chambers discharges cuttings and a second pneumatic cylinder for moving said multi-chamber receptacle to a second position wherein said second at least one of said receptacle chambers collects cuttings and said at least one of said receptacle chambers discharges cuttings.

14. A soil sampling apparatus usable with a drilling rig having a rotating drill for boring a borehole in soil and producing drilling cuttings, said soil sampling apparatus comprising:
- a sample container;
- a multi-chamber receptacle defining a plurality of receptacle chambers for receiving drilling cuttings and positioned so drilling cuttings are discharged into said sample container, said receptacle including means for simultaneously receiving drilling cuttings and discharging drilling cuttings into said sample container;
- actuating means for laterally moving said receptacle between a first position wherein at least one of said receptacle chambers collects cuttings and a second at least one of said receptacle chambers discharges cuttings and a second position wherein said second at least one of said receptacle chambers collects cuttings and said at least one of said receptacle chambers discharges cuttings;
- control means for controlling the movement of said receptacle.

15. The soil sampling apparatus of claim 14, wherein said actuating means comprises at least one servomechanism.

16. The soil sampling apparatus of claim 15, wherein said at least one servomechanism includes a first servomechanism for moving said receptacle to the first position and a second servomechanism for moving said receptacle to the second position.

17. The soil sampling apparatus of claim 14, wherein said actuating means comprises at least one pneumatic cylinder.

18. The soil sampling apparatus of claim 17, wherein said at least one pneumatic cylinder includes a first pneumatic cylinder for moving said receptacle to the first position and a second pneumatic cylinder for moving said receptacle to the second position.

* * * * *